United States Patent [19]

Stärk et al.

[11] 3,972,858

[45] Aug. 3, 1976

[54] PROCESS FOR THE PREPARATION OF CHOLERAGEN

[75] Inventors: Joseph Stärk, Marburg an der Lahn; Oswald Zwisler, Marbach near Marburg an der Lahn, both of Germany

[73] Assignee: Behringwerke Aktiengesellschaft, Marburg an der Lahn

[22] Filed: Dec. 19, 1974

[21] Appl. No.: 534,278

[30] Foreign Application Priority Data
Dec. 22, 1973 Germany............................ 2364317

[52] U.S. Cl. .............................. 260/112 R; 424/92
[51] Int. Cl.² ..................... A61K 39/02; C07G 7/00
[58] Field of Search.............. 260/112 R; 424/92, 88

[56] References Cited
UNITED STATES PATENTS
3,686,395   8/1972   Stephan ............................ 424/101

OTHER PUBLICATIONS
J. Exptl. Med.; 1969, Finkelstein et al., pp. 185–202.
Science, vol. 175, 1972, Finkelstein et al.

*Primary Examiner*—Howard E. Schain
*Attorney, Agent, or Firm*—Curtis, Morris & Safford

[57] ABSTRACT

The invention relates to a process for preparing choleragen, which comprises adding silicic acid to a solution containing choleragen, stirring the suspension, separating the silicic acid, treating for elution with an aqueous salt or buffer solution, and separating the choleragen-containing eluate from the silicic acid.

**12 Claims, No Dr

PROCESS FOR THE PREPARATION OF CHOLERAGEN

The invention relates to a process for the preparation of choleragen which is suitable for application on an industrial scale.

It is generally recognized that the diarrhea associated with the cholera disease is caused by an exoenterotoxin of the chloera pathogen *Vibrio cholerae*. This cholera toxin, also termed as choleragen, is, via a complex mechanism, the reason for the hypersecretion of water and salts which is known in the case of cholera and characteristic of the disease.

Within the scope of considerations to combat the cholera by immune prophylaxis choleragen has become most important.

The commercial cholera vaccines consist of a suspension of dead *Vibrio cholerae*. It is detectable that the immunity produced after parenteral injection of these vaccines into the test person has almost exclusively an anti-bacterial character. Field tests have proved that a parenteral vaccination with germ-containing vaccines imparts a protection against cholera for several months.

Animal tests have shown that a detoxified choleragen, when administered parenterally or orally, led to a resistance of the animals to virulent cholera vibrios. The immunity which diminished only in the course of several months could be restored by oral administration of the detoxified choleragen. Though there are results opposite to these, the latter show an increasing need for a process to obtain choleragen which can be carried out on an industrial scale.

The processes hitherto known for obtaining choleragen have been developed as laboratory processes and can be transferred to the industrial scale only to a limited extent. The processes designated as being carried out on an industrial scale are characterized by complicated precipitation phases with ethanol at low temperatures and by different chromatographic measures. Particularly, the most difficult problem appearing in the preparation of choleragen cannot be overcome with the aid of these methods, i.e., that the substance desired is generally available in a very small concentration in a solution having a considerable ionic strength, the culture filtrate of the cholera vibrio.

When trying to resolve this problem aluminum hydroxide was used in the form of gel for the adsorption of the choleragen. The relatively large volume per weight unit and the consistency of the adsorbent, however, leads to disadvantages with regard to working up.

It has now been found that silicic acid, especially that prepared synthetically by hydrolysis of silicium tetrachloride, is able to bind the choleragen from choleragen-containing solutions, especially from the culture filtrate of a choleragen-binding vibrio cholerae, and that the choleragen can be eluted again. If desired, the choleragen isolated by this process in a high concentration may be subjected to further purification by ion exchange chromatography and/or molecular sieve techniques.

Thus, the present invention relates to a process for preparing choleragen, wherein silicic acid is added to a solution containing choleragen, the suspension is stirred, the silicic acid is separated, treated, for elution, with an aqueous salt or buffer solution, the eluate containing choleragen is separated from the silicic acid and, if desired, further purified by ion exchange chromatography and/or molecular sieve techniques.

The invention further relates to a choleragen prepared according to this process.

It is particularly advantageous to use as an adsorbent a silicic acid composition which is prepared by the hydrolysis of silicon tetrachloride in an oxyhydrogen gas flame, has a content of $SiO_2$ of more than 99 %, consists of amorphous globular particles, and has an average diameter of 5 to 50 millimicrons and a surface of more than 30 $m^2$ per gram (measured according to Brunauer, Emmet and Teller, J. Amer. Chem. Soc. 60, 309–319, 1938), as it is commercially available for example as Aerosil$^{(R)}$ of Messrs. Degussa, Frankfurt. There is no reason, however, why silicic acids having different compositions should not be used for the purpose indicated, if their decisive characteristic is that they have a relatively large surface, as related to the weight, and have SiOH-groups on the surface.

A preferred method for obtaining the choleragen is the treatment of the choleragen-containing culture filtrate with a silicic acid, the surface of which comprising 50 ± 15 $m^2$ per gram of silicon dioxide. In amounts of 1 to 5 grams/liter, preferably 2 grams/liter, this adsorbent binds the choleragen reversibly in choleragen-containing solutions, especially in culture filtrates, in a pH-range of 6.0 to 7.0, preferably at pH 6.5.

The same conditions of adsorption are found in choleragen-containing solutions whose freezing point, reduced by the addition of electrolytes, has been adjusted to a level comparable to that of a culture filtrate of *Vibrio cholerae*. But on principle the silicic acid should be used as adsorbent for each choleragen-containing solution; in this case the rule is that a low pH value and a low conductivity of the solution favors the linking of the choleragen to the adsorbent, whereas a high pH-value and a high conductivity of the solution favors the separation of the choleragen from the adsorbent.

Silicic acids having a larger surface have a stronger binding capacity to choleragen than those having smaller surfaces. In the case of pH-values considerably below the range indicated the adsorption from culture solutions is not reversible, i.e. a desorption can only be carried out with losses of yield and antigenicity, whereas in the case of pH-values clearly above the range indicated a bond of substantial parts of the choleragen does no longer take place.

For elution there are considered aqueous salt or buffer solutions suitable for eluting choleragen from silicic acid. Suitable in this sense are aqueous solutions whose electrolytes contain negative ions of weak acids and/or maintain sufficiently constant the pH-range of 7.0 to 9.0. Therefore, for recovering the choleragen, solutions of sodium acetate or sodium citrate or buffer mixtures usual in encymology such as trishydroxymethylaminomethane phosphoric acid are used as eluting solutions. Elution is preferably carried out at pH 8.5. The conductivity of the elution solutions is at least 5, preferably 15 millisiemens.

To increase the yield it is advantageous to add to the elution solution electrolytes, preferably in the form of strongly dissociating salts. The necessary amount of the additive depends on the pH-value of the elution solution; that means that a high pH-value requires less electrolyte than a low pH-value if the same yield shall be reached. The concentration of sodium chloride indicated as an example is between 1 and 15 % at pH 8.5 and when using a 0.1 M tris-hydroxymethylaminomethane-phosphoric acid buffer between 5 and 7.5 %. The choleragen can be eluted with a yield of 70 to 90 %. The elution volume may be a fraction of the original volume; thus, the adsorption step of the invention is particularly suitable for the reduction of the big volumes on the industrial scale to amounts easier to treat.

The eluted choleragen may be further concentrated, preferably with the aid of membranes impermeable for choleragen. It may be dialyzed for the reduction of the salt content and for conversion into other buffer mixtures and lyophilized in suitable buffer mixtures. If desired, it may be further purified.

After the eluted choleragen has been concentrated with the aid of membrane filters and freed from mucous or viscous contaminations by high-speed centrifugation, it may be fractioned over a molecular sieve gel on the basis of polyhydroxy compounds such as dextrane, cellulose and agarose or suitable plastics such as polyacrylamide, preferably in a column filled with dextrane cross-linked with epichlorohydrine, the sieving hold back limit of which is at molecular weights of about 150 000, for example Sephadex[(R)] G 150 of Messrs. Pharmacia, Uppsala. The fraction containing the choleragen in a high purity may be obtained by collecting the fractions containing this choleragen (test according to the methods described below) and freeze-dried after dialysis against a suitable buffer system.

The starting material for obtaining choleragen according to the process of the invention is preferably a sterile filtrate of a culture of a Vibrio cholerae known from literature as choleragen forming agent, for example *Vibrio cholerae* 569 B Inaba, *Vibrio cholerae* 12 Ogawa, *Vibrio cholerae* B 1307 and other vibrios, which has also been multiplied in suitable semi-synthetic culture solutions also described in literature. During this process choleragen is deposited in the culture solution.

Before extracting the culture filtrate it is suitable, as a precautionary measure, in order to protect the operational personnel from a cholera infection, to inactivate the culture. Not all the antibacterial agents capable of killing the cholera vibrio, are suitable. Beta-propiolactone, for example, causes damages in the choleragen. Furthermore, it cannot be forseen whether the inactivating agent used will interfere with the adsorbent in the way that the choleragen is not adsorbed.

The process of the invention to adsorb choleragen from culture filtrates can be carried out particularly well, if the inactivation of *Vibrio cholerae* has taken place for example by the action of 0.2 to 0.9, preferably 0.5 % of phenol, or of 0.05 to 0.3, preferably 0.1 % of 2-ethoxy-6,9-diamino-acridine lactate. However, the inactivation of the germs or the reduction of the number of germs can also be achieved by other known bactericidal agents having a structure comparable to one of the substances mentioned. The inactivation of the germs, however, is not necessary for the adsorption of the choleragen from the sterile filtrate. If, in the case of corresponding technical measures the culture filtrate has been obtained without previous inactivation of the vibrios, the adsorption may be effected by silicic acid in the same manner described according to the invention.

The measuring and proof of the content of choleragen in solutions is effected on one hand immunologically with the aid of a haemagglutination inhibition test, as described by Finkelstein et al. in 1970 for the special case of the choleragen, on the other by the proof of an increased permeability of the fabric by the choleragen by measuring the so-called blue dyeing dosis.

Haemagglutination inhibition test (HAI) for the determination of choleragen:

A suspension of erythrocytes charged with choleragen according to Finkelstein (1970) is tested with regard to reactivity against a dilution series of anti-choleragen serum of the rabbit. For this purpose a dilution series of the anti-serum is prepared on a microtiter plate and 0.025 ml of the suspension of erythrocytes is added in each case to 0.05 ml of each dilution. The plate is shaken for some seconds on the vibrator. After one to two hours the final point to be read off is the last dilution which showed a good agglutination. For the haemagglutination inhibition test (HAI) the dilution of the anti-serum is chosen which is eight times lower than the final dilution read off; i.e. when reading off for example 1: 3200 a dilution of 1 : 400 is chosen.

On a microtiter plate dilution series (0.05 ml) of the 1 to 80 µg/ml choleragen-containing solution to be tested and a standard sample of 20 µg/ml of choleragen are prepared. To each solution 0.025 ml of the concentration previously determined of the antiserum is added. The mixture is shaken, allowed to stand for one hour and finally 0.025 ml of the suspension of erythrocytes charged with choleragen is added and shaken again. After 1 to 2 hours an inhibition of the agglutination in the case of the low dilutions of the choleragen samples to be examined and an agglutination in the case of the high dilutions can be seen.

For analysis the HAI titer of the sample is put into relation with the HAI titer of the 20 µg/ml choleragen standard which is mostly between 1:32 and 1:64.

Determination of the blue dyeing dose of choleragen with the intracutaneous test on guinea pigs:

Suitable dilution series are prepared in two phases from choleragen.

In the case of albino guinea pigs the lateral abdominal walls are depilated. Six intracutanous injections of 0.1 ml each of the choleragen dilutions are administered to each guinea pig. After 18 to 20 hours 1 ml of a 1 % Evans Blue solution in an isotonic solution are administered intravenously. The diameters of the dyed zones are measured after 1 hour. One blue dyeing dosis is the amount of choleragen which produces the blue color within an area of 8 × 8 mm. The blueing dosis per ml amounts to 10 times the reciprocal value of the dilution which has produced a 8 × 8 mm area.

The following Examples illustrate the invention.

EXAMPLE 1:

300 Liters of a choleragen-containing culture filtrate obtained after inactivation with 0.5 % of phenol from the culture Cholera Inaba 569 B and after subsequent centrifugation over a separator of Messrs. Westphalia, was cooled to +15°C in a vessel provided with a cooling jacket and a stirrer. Then 600 g of Aerosil (R) 0X50 (silicic acid, 50 m$^2$ surface per gram, of Messrs. Degussa) suspended in 10 l of distilled water were added while stirring. The pH-value of the suspension which was 7.8, was adjusted to 6.5 by addition of 1N hydrochloric acid. Stirring was continued for 3 to 4 hours and then the stirrer was stopped. Within 8 hours the Aerosil[(R)] 0x50 formed a deposit so that an excess of about 270 l free from Aerosil could be siphoned off. The remaining 30 l suspension was centrifuged with a continuous centrifuge. The sediment obtained having a volume of 2.5 l was resuspended, while stirring, in 15 l of the following buffer:

0.1 M of phosphoric acid
0.06 M of trishydroxymethylamino-methane
0.001 M of ethylene-diamino-tetra-acetic acid and adjusted to pH 8.5 with NaOH.

After suspending 1125 g of sodium chloride were added; i.e. 7.5 % calculated on 15 l of buffer solution, pH 8.5. The suspension was stirred for 20 hours at 20°C and centrifuged for 45 minutes at 9000 g. 15 l of a centrifuged excess containing the choleragen were obtained.

This excess was diluted to 30 l with distilled water and concentrated to 3 liters with an ultrafilter. The ultrafilter concentrate was then dialysed for 4 hours against current water free from salt and then against 20 l of the following buffer:

5 mM of phosphoric acid 0.5 mM of ethylene-diamino-tetra-acetic acid adjusted to pH 8.0 with 1N sodium hydroxide solution.

The dialysed solution was then lyophilized.

The lyophilized product was then dissolved in 500 ml of distilled water and centrifuged for 20 hours at 18,000 g and a temperature of +5°C.

The excess resulting from centrifugation was poured onto a column (30 cm/50 cm) filled with Sephadex [(R)] G - 150 (Pharmacia, Uppsala). The Sephadex [(R)] G - 150 was equilibrated with the following buffer, i.e. washed several times:

0.1 M of trishydroxy-methylamino-methane 0.1 M of sodium chloride 0.5 mM of ethylene diamino-tetra-acetic acid adjusted to pH 8.0 with hydrochloric acid 0.02 % of sodium azide.

Elution was effected with the buffer also used for equilibration. The adsorption of the eluate at 280 nm was measured in a flow photometer. Two peaks were observed. The high-molecular fraction, represented by the first peak, did not contain any choleragen. The choleragen was found again in the second peak. The choleragen-containing second fraction was concentrated to about 1 liter and then dialysed against the following buffer:

0.02 M of phosphoric acid 0.5 mmoles of ethylene-diamino-tetraacetic acid adjusted to pH 8.0 with 1N hydrochloric acid.

Then the solution was lyophilized.

Yield: 1.76 g of pure product.

EXAMPLE 2:

300 Liters of a culture filtrate containing choleragen, which was obtained by inactivation of the culture Cholera Inaba 569 with 0.1 % of 2-ethoxy-6,9-diamino-acridine-lactate and subsequent centrifugation of the culture over a separator of Messrs. Westphalia were mixed, as described in Example 1, with Aerosil, with the modification that first 300 g of Aerosil[(R)] 0x50, suspended in 2 liters of water, were added and 1 hour later another 600 g of Aerosil[(R)] 0x50, suspended in 8 l of water, were added. Furthermore, during the desorption of the choleragen of Aerosil[(R)] 0x50 2250 g instead of 1125 g of sodium chloride were added.

The yields and degrees of purity of the individual purification steps correspond to a large extent to those of Example 1.

EXAMPLES 3, 4 and 5:

250 ml in each case of a culture filtrate of the *Vibrio cholerae* Inaba 569 B concentrated at the ultrafilter by the threefold amount were mixed, while stirring,

| | | |
|---|---|---|
| according to Ex. 3: | with 1 g of Aerosil (200 $m^2$ surface per g) | 200 V |
| according to Ex. 4: | with 1 g of Aerosil (80 $m^2$ surface per g) | MOX 80 |
| according to Ex. 5: | with 1 g of Aerosil (50 $m^2$ surface per g) | OX 50 | and the pH-value of the suspension was adjusted to 6.5 with 1N hydrochloric acid. The suspension was stirred for 3 hours at +15°C. After another 15 hours it was stirred for 1 hour at 6000 g. The sediments of the centrifugations were resuspended in 30 ml of the phosphoric acid described in Example 1, tris(hydroxymethyl)-aminomethane, EDTA-buffer of pH 8.5, and to each suspension 2.25 g of sodium chloride were added. Stirring was continued for 20 hours and the mixture was centrifuged for 45 hours at 9000 g. The values resulting from the choleragen worked up in the pH-8.5 eluates thus obtained are compiled in the Table.

| Choleragen fraction | amount l | choleragen according to HAI mg/l | total amount of choleragen mg | yield % |
|---|---|---|---|---|
| culture filtrate concentrated 3 times | 0.250 | 30 | 7.50 | (100) |
| Eluates according to | | | | |
| Example 3 | 0.033 | 80 | 2.64 | 35 |
| Example 4 | 0.028 | 80 | 2.64 | 30 |
| Example 5 | 0.023 | 320 | 7.35 | 98 |

What we claim is:

1. A process for preparing choleragen, which comprises adding silicic acid to a solution containing choleragen, stirring the suspension, separating the silicic acid, treating for elution with an aqueous salt or buffer solution, and separating the choleragen-containing eluate from the silicic acid.

2. The process as defined in claim 1, wherein the choleragen obtained is further purified by ion exchange chromatography and/or molecular sieve techniques.

3. The process as defined in claim 1, wherein the silicic acid is obtained by hydrolysis of silicon tetrachloride in an oxyhydrogen flame.

4. The process as defined in claim 1, wherein the silicic acid has a content of $SiO_2$ of more than 99 %.

5. The process as defined in claim 1, wherein the silicic acid consists of amorphous globular particles having an average diameter of 5 to 50 millimicrons.

6. The process as defined in claim 1, wherein the silicic acid has a surface of more than 30 $m^2$ per gram.

7. The process as defined in claim 6, wherein the silicic acid has a surface of 50±15 m² per g of silicon dioxide.

8. The process as defined in claim 7, wherein the silicic acid is present in an amount of 1 to 5 g per liter of solution containing choleragen and said solution has a pH of from 6.0 to 7.0.

9. The process as defined in claim 1, wherein the silicic acid to which the choleragen is bound is eluted with an aqueous solution having a conductivity of at least 5 mS and a pH-value of from 7.0 to 9.0.

10. The process as defined in claim 1, wherein the solution containing choleragen is a culture filtrate of a choleragen-forming *Vibrio cholerae*.

11. The process as defined in claim 10, wherein the cholera vibrios in the culture filtrate are inactivated with 0.2% to 0.9% of phenol.

12. The process as defined in claim 10, wherein the cholera vibrios in the culture filtrate are inactivated with 0.05 to 0.3% of 2-ethoxy-6,9-diamino-acricine lactate.

* * * * *